United States Patent [19]

Buxton et al.

[11] Patent Number: 4,755,378

[45] Date of Patent: Jul. 5, 1988

[54] IODOPHOR-CONTAINING SUPPOSITORY

[75] Inventors: Ian R. Buxton, Cambridgeshire; Stewart T. Leslie, Cambridge; Sandra T. A. Malkowska, Cambridge; Joanne Marchant, Cambridge, all of England

[73] Assignee: Euroceltique, S.A., Luxembourg, Luxembourg

[21] Appl. No.: 890,730

[22] Filed: Jul. 30, 1986

[30] Foreign Application Priority Data

Aug. 17, 1985 [GB] United Kingdom ............... 8520664

[51] Int. Cl.$^4$ ...................... A61K 31/79; A61K 33/18
[52] U.S. Cl. ...................... 424/80; 424/150; 424/433; 514/966; 514/967
[58] Field of Search ............ 424/80, 150, 433; 514/966, 967

[56] References Cited

U.S. PATENT DOCUMENTS

| | | | |
|---|---|---|---|
| 2,975,099 | 3/1961 | Goyan et al. | 424/433 X |
| 3,234,091 | 2/1966 | Lang et al. | 424/433 |
| 4,576,818 | 3/1986 | Shetty | 424/150 |

*Primary Examiner*—Leonard Schenkman
*Attorney, Agent, or Firm*—Steinberg & Raskin

[57] ABSTRACT

Iodophor-containing suppositories are provided with improved rate of iodine release from the suppository. The suppository composition comprises an iodophor, a water soluble suppository base, at least one water soluble sugar having a molecular weight of between about 90 and 550, and water in an amount of at least about 30% by weight. The molecular weight of the sugar is preferably between about 150 and 370. The preferred iodophors are providone iodine and polydextrose iodine. The preferred suppository bases are gelling polysaccharides and the preferred sugars are monosaccharides, disaccharides and sugar alcohols. The rate of iodine release is improved because of the high concentration of water together with the presence of the low molecular weight sugar.

13 Claims, No Drawings

IODOPHOR-CONTAINING SUPPOSITORY

BACKGROUND OF THE INVENTION

Suppositories containing an iodophor such as povidone iodine, are known. The known suppositories consist of povidone iodine and polyethylene glycol (M. Wt. about 1000). Although the level of iodine activity achieved by these suppositories is acceptable, it could usefully be improved.

Such an improvement would be particularly useful in the case of iodophor-containing vaginal suppositories, but would also be advantageous in the case of rectal suppositories in which antibacterial agents are added to supplement the action of, for example, anti-inflammatory agents.

SUMMARY OF THE INVENTION

It is accordingly a primary object of the present invention to provide iodophor-containing suppositories with an improved level of iodine activity.

It is another object of the present invention to provide iodophor-containing suppository compositions which can be used for vaginal suppositories (pessaries) and which provide improved levels of iodine activity.

It is yet another object of the present invention to provide iodophor-containing suppositories with improved rate of iodine release from the suppository.

Other objects and advantages of the present invention will be apparent from further reading of the specification and of the appended claims.

With the above and other objects in view, the present invention mainly comprises a suppository composition comprising an iodophor, a water soluble suppository base, at least one water soluble low molecular weight sugar, and water in an amount of at least about 30% by weight. The suppository composition can be used for rectal suppositories and for vaginal suppositories.

It should be noted that in the discussion of this invention, the term "level of iodine activity" refers to the concentration of equilibrium (free) iodine at the site of iodophor action. This is of considerable importance because it is the free iodine that is responsible for the microbiocidal action of iodophors.

It is preferred that the concentration of water in the suppository be about 40-80% by weight, and most preferably about 50-70% by weight.

It has been found that by adding at least one water soluble low molecular weight sugar to the suppository composition along with a high proportion of water, the level of iodine activity is greatly improved in comparison with the level achieved by known iodophor suppositories which contain neither water nor low molecular weight sugar.

The preferred iodophors used for the suppositories of the invention are the water-soluble, physiologically-acceptable complexes of iodine with organic polymers, in which the germicidal and microbiocidal activity of elemental iodine is maintained. Examples of such iodophors include combinations of elemental iodine with detergent polymers, such as nonylphenoxy poly (ethylenoxy) ethanol and undecoylium chloride. In a particularly preferred embodiment of the present invention, however, the iodophor is a complex of iodine with a suitable non-ionic, non-detergent (non-surface active), water-soluble organic polymer, such as polyvinylprroli done (providone), polydextrose or a copolymer of sucrose and epichlorohydrin. Of these non-ionic, non-detergent organic polymers, povidone and polydextrose are especially preferred.

Polyvinylpyrrolidone is a non-ionic, non-detergent water soluble, organic polymer that is characterised by an unusual complexing ability, by its colloidal properties and by its physiological inertness. Its iodine complex, polyvinylpyrrolidone (povidone) iodine, is a well known iodophor that is a highly effective germicide, providing a broad spectrum of microbiocidal action against virtually all microbes.

Povidone iodine and the preparation thereof is described in U.S. Pat. No. 2,739,922.

Polydextrose iodine, which is prepared from polydextrose and iodine is described in U.S. Pat. No. 4,576,818. Any polydextrose iodine described in said patent can be used for the purposes of the present invention.

The amount of iodine incorporated in the iodophors used in the suppositories of the present invention will be determined by, amongst other factors, the amount of iodophor present in the suppository and the required germicidal strength of the suppository.

Preferably, iodine will constitute between 1 and 20% (by wt.), especially between 2 and 16% (by wt.), most especially between 2 and 12% (by wt.) of the iodophor dry weight.

Similarly, the concentration of iodophor in the suppository will depend on germicidal strength required. In addition, iodophor concentration will also be determined by the iodophor employed, the amount of iodine in the iodophor, the propensity of the iodophor to cause irritation, the rate of iodine loss (when the suppository is in use) and the length of suppository use contemplated. In order to treat most disorders, the suppository should contain sufficient iodophor to afford a concentration of available (thiosulphate titratable) iodine within the suppository of between 0.1 and 5% (by wt.), especially between 0.5 and 1.5% (by wt.).

The suppository base must be water-soluble. It must hold water whilst retaining its mechanical strength. The base is chosen so as to give a suppository that:
  (i) is easily inserted into the body, without incidental tissue trauma or pain, and
  (ii) after insertion, disintegrates readily, by dissolving, dispersing or, melting, thereby distributing the iodophor within the vaginal or rectal cavity.
  (iii) Preferably the base is also chosen so as to draw moisture to the site of action within the vaginal or rectal cavity and thereby further activate the iodophor.

Preferably the present suppository base comprises a water soluble gelling polymer (gelling in aqueous medium), such as gelatin, polyoxyethylene glycol, polymerized ethylene oxide derivatives of glycols, mixtures of polyoxyethylene glycols and polycyclohexoses (see Canadian Pat. No. 825687), soya protein and its derivatives, fatty acid glycerides, or, which is most preferred, a polysaccharide, such as agar, an alginate salt, a cellulose derivative or carrageenan. In a particularly preferred embodiment, the suppository base is sodium alginate.

The water soluble, low molecular weight sugar should preferably have a molecular weight between about 90 and 550, especially between 150 and 370. The sugar may be a monosaccharide, such as the hexoses, glucose, fructose, galactose and mannose, a disaccharide, such as sucrose and lactose, or a sugar alcohol, such as mannitol, sorbitol and xylitol. The presence of the sugar, especially in combination with the gelling polymer base, facilitates the formation of the suppository, giving it enhanced mechanical rigidity. In addition to this property, the sugar will also draw moisture to the site of action in the vaginal or rectal cavity and thereby activate the iodophor.

The present suppository preferably further comprises at least one of:

(i) A water-soluble polyalcohol that is non-toxic, lubricating and demulcent, Examples include propylene glycol or, which is preferred, glycerol. In addition to acting as a lubricant and demulcent, the polyalcohol will also draw moisture to the action in the vaginal or rectal cavity and, like the sugar, activate the iodophor.

(ii) A surfactant, especially an anionic or non-ionic surfactant. The presence of a surfactant reduces the surface tackiness of the suppositories, making them easier to remove from their packaging and, therefore, to handle. Examples of suitable surfactants include Tween (Trade Mark) and Cremophor (Trade Mark) surfactants, especially Cremophor RH40 (Trade Mark BASF), which is a glycerol polyethylene glycol oxystearate surfactant.

The concentration of the constituent or consituents of the present suppository base will be determined by, amongst other factors:

(a) The pH required at the site of action. This pH should be close to the pH in the vaginal or rectal cavity to be treated (to avoid irritancy) and should allow good microbiocidal activity. A pH between 3 and 8, especially between 3.5 and 6 will be acceptable for most therapeutic applications, (b) The intended use of the suppository.
(c) The rigidity required for the suppository.
(d) The iodophor release characteristics required.
(e) The amount of water and iodophor to be employed in the suppository.

Preferred concentrations (given as a % of total suppository weight) for the constituent or constituents of the present suppository are Gelling polymer: at least 2%, especially 2–30%
Polyalcohol: 0–25%, especially 2–15%
Sugar: 5–50%, especially 10–35%
Surfactant: 0–10%, especially 1–5%

Suppositories of the present type may be manufactured by the hot pour technique. This involved the pouring of the suppository composition, in fluid form, into a suitable mould, which is then cooled below the solidification point of the composition to give a suppository of the desired size and shape. Alternative methods of suppository formation employing gelling polymers, such as agar and sodium alginate, will be known to those skilled in the art.

The precise size and shape of the suppository will be determined primarily by the use contemplated. Generally, a longitudinally shaped body, such as a cylindrical, conical, tapered or egg shape, and a dose form weight between 1 and 5 gm. will be suitable for most applications.

DESCRIPTION OF PREFERRED EMBODIMENTS

The following description and examples are given to further illustrate the present invention. The scope of the invention is not, however, meant to be limited to the specific details of the examples.

Starting Materials (i) Polydextrose Iodine (4% concentration)

Deionized water (31.2 g) was placed in a stainless steel vessel fitted with an efficient mixer. With vigorous stirring, polydextrose (46.0 g., Pfizer, Chemical Division, NY) was slowly added (in a portionwise manner). Once the polydextrose was dissolved in the water, potassium iodide (18.6 g., USP) was added and the vigorous stirring was continued. The potassium iodide was allowed to dissolve to give a clear solution and then iodine (4.2., USP) was slowly added, once again with vigorous stirring. The stirring was continued until the amount of titratable iodine present, in samples taken from the reaction mixture, remained constant over a period of one hour. Finally the reaction mixture was filtered through a 200 mesh stainless steel rigimesh filter. The final solution was opaque and red-brown in color. The polydextrose-iodine complex in the solution had an available (titratable) iodine content of about 4% by (w/w).

(ii) Polydextrose Iodine (7% available iodine)

The procedure of (i) above was followed except that the proportions of the components were adjusted to give a polydextrose iodine solution having an available iodine content of about 7% by (w/w).

EXAMPLE 1

Glycerol (0.175 g., BP), Cremophor RH40 (0.35), (which is the trademark for a brand of glycerol polyethyleneglycol oxystearate) and distilled water (1.7 mL) were mixed. Mannitol (0.35 g., BP) was then dissolved in the solution. Gelatin (0.7 g, 250 g Bloom, BP) was then dispersed in the solution, after which the solution was heated to 50°. Once the gelatin had dissolved, the mixture was allowed to cool to 40°. Polydextrose iodine solution (0.55 g of (i) above) was thoroughly mixed into the solution, which was then dispensed into a cylindrically shaped mould. Finally, the composition was allowed to cool to ambient temperature, to produce a cylindrically shaped vaginal suppository, weighing 3.5 g and containing 20 mg of available iodine.

EXAMPLE 2

A vaginal suppository having the following ingredients was prepared by the method described in Example 1,

|  | % (w/w) |
| --- | --- |
| Polydextrose iodine (7% available iodine) | 8.163 |
| Mannitol | 15.00 |
| Gelatin | 20.00 |
| Cremophor RH40 | 1.00 |
| Glycerol | 5.00 |
| Distilled Water | 50.837 |

The vaginal suppository produced weighed 3.5 g. and contained 20 mg. of available iodine.

EXAMPLE 3

A vaginal suppository having the following ingredients was prepared by the method described in Example 1,

|  | % (w/w) |
| --- | --- |
| Povidone iodine | 5.195 |

-continued

| | % (w/w) |
|---|---|
| (11% available iodine) | |
| Gelatin | 25.00 |
| Mannitol | 10.00 |
| Glycerol | 5.00 |
| Cremophor RH40 | 2.00 |
| Distilled Water | 52.805 |

EXAMPLE 4

Adipic acid (1.3 g was dispersed in polydextrose iodine (8.2 g., of (ii) above). Calcium hydrogen phospate (0.1 g.) was then dispersed in the PDI/adipic acid dispersion.

Separately, sodium alginate (3.0 g.), Manucol DM, (which is the trademark for a brand of sodium alginate) was dissolved in water (51.8 g.), by gradually heating the water to 70°. Sucrose (28.0 g.), glucose (7.0 g.) and sodium meta-phospate (0.6 g.) were dissolved in the sodium alginate solution, again at 70°. The alginate solution was then cooled to 50°. 0.34 g. of the PDI containing suspension was placed in a preformed foil mould. To this was added 3.16 g. of the alginate solution. When filling was complete, the foil moulds were heat sealed and then cooled to 50° for 4 hours.

| | |
|---|---|
| PDI | 0.02 g. |
| Sodium alginate | 0.105 g. |
| Glucose | 0.245 g. |
| Sucrose | 0.98 g. |
| Sodium metaphospate | 0.021 g. |
| Calcium hydrogen phospate | 0.0035 g. |
| Adipic acid | 0.0455 g. |
| Water | 2.08 g. |

While the invention has been described with respect to particular suppository compositions, it is apparent that the variations and modifications of the invention can be made without departing from the spirit or scope thereof.

What is claimed is:

1. A suppository formed of at least one iodophor in an amount and with sufficient iodine concentration to provide germicidal activity, a water-soluble suppository base and at least one water-soluble sugar or sugar alcohol having a molecular weight between about 90 and 550 in amounts sufficient to provide rigidity to the suppository, and water in an amount of at least about 30% by weight, wherein the water and sugar or sugar alcohol increases the level of iodine activity.

2. Suppository according to claim 1 wherein the amount of water is between about 40 and 80% by weight.

3. Suppository according to claim 1 wherein the amount of water is between about 50 and 70% by weight.

4. Suppository according to claim 1 wherein the iodophor is povidone iodine or polydextrose iodine.

5. Suppository according to claim 1 wherein the suppository base is a water soluble, gelling polysaccharide.

6. Suppository according to claim 1 wherein the suppository base is agar, an alginate salt, a cellulose derivative or carrageenan.

7. Suppository according to claim 1 wherein the molecular weight of the sugar is between about 150 and 370.

8. Suppository according to claim 1 wherein the sugar is a monosaccharide or a disaccharide.

9. Suppository according to claim 1 wherein the water soluble sugar or sugar alcohol is glucose, fructose, galactose, mannose, sucrose, lactose, mannitol, sorbitol or xylitol.

10. Suppository according to claim 1 wherein the concentration of sugar or sugar alcohol is between about 5 and 50% by weight.

11. Suppository according to claim 1 wherein the concentration of sugar or sugar alcohol is between about 10 and 35% by weight.

12. Suppository according to claim 1 and also including a water soluble polyalcohol.

13. Suppository according to claim 1 in the form of a vaginal suppository.

* * * * *